(12) United States Patent
Xu

(10) Patent No.: US 10,190,763 B2
(45) Date of Patent: Jan. 29, 2019

(54) LED PURIFYING AND ENERGY-SAVING LAMP

(71) Applicant: DONGGUAN YINGHUI LIGHTING CO., LTD., Dongguan, Guangdong (CN)

(72) Inventor: Shuisheng Xu, Guangdong (CN)

( * ) Notice: Subject to any disclaimer, the term of this patent is extended or adjusted under 35 U.S.C. 154(b) by 0 days.

(21) Appl. No.: 15/340,129

(22) Filed: Nov. 1, 2016

(65) Prior Publication Data

US 2017/0130952 A1  May 11, 2017

(30) Foreign Application Priority Data

Nov. 6, 2015  (CN) ..................... 2015 2 0888354 U

(51) Int. Cl.
| | | |
|---|---|---|
| *F21V 33/00* | (2006.01) | |
| *F21V 17/10* | (2006.01) | |
| *A61L 9/22* | (2006.01) | |
| *F21V 1/02* | (2006.01) | |
| *F21V 29/77* | (2015.01) | |
| *F21V 29/90* | (2015.01) | |
| *F21V 23/06* | (2006.01) | |
| *F21V 29/83* | (2015.01) | |
| *B01D 53/32* | (2006.01) | |
| *F21Y 115/10* | (2016.01) | |

(52) U.S. Cl.
CPC ............ *F21V 33/0064* (2013.01); *A61L 9/22* (2013.01); *B01D 53/32* (2013.01); *F21V 1/02* (2013.01); *F21V 17/10* (2013.01); *F21V 23/06* (2013.01); *F21V 29/77* (2015.01); *F21V 29/83* (2015.01); *F21V 29/90* (2015.01); *A61L 2209/12* (2013.01); *B01D 2259/818* (2013.01); *F21Y 2115/10* (2016.08)

(58) Field of Classification Search
CPC ...... F21V 33/0064; F21V 29/83; F21V 29/77; F21V 1/02; F21V 29/90; F21V 23/06; F21V 17/10; A61L 9/22; A61L 2209/12; B01D 53/32; B01D 2259/818; F21Y 2115/10

See application file for complete search history.

(56) References Cited

U.S. PATENT DOCUMENTS

2009/0291029 A1 * 11/2009 Ogasawara ............... A61L 9/18
422/122
2013/0175454 A1 * 7/2013 Cooper ................... C02F 1/325
250/435

* cited by examiner

*Primary Examiner* — Tracie Y Green
(74) *Attorney, Agent, or Firm* — Alan D. Kamrath; Kamrath IP Lawfirm, P.A.

(57) ABSTRACT

An LED purifying and energy-saving lamp comprises a lamp body, a heat radiator, a light source assembly and an air purifying device, wherein the lamp body comprises a main body portion, an overflow table and a plurality of connecting blocks; the heat radiator, the light source assembly and the air purifying device are provided in the main body portion; the air purifying device is provided above the heat radiator; the light source assembly is provided inside the heat radiator; the upper part of the main body portion is connected to the bottom edge of the overflow table via the plurality of connecting blocks; the main body portion, the overflow table and the connecting blocks define a plurality of air outlets; and a shunting spur is convexly provided at the bottom of the overflow table toward the interior of the main body portion.

10 Claims, 2 Drawing Sheets

LED PURIFYING AND ENERGY-SAVING LAMP

FIELD OF THE INVENTION

The present patent relates to an illuminating lamp, in particular to an LED purifying and energy-saving lamp.

BACKGROUND OF THE INVENTION

The traditional LED lamp is a very common illuminating tool which only has an illuminating function, however, an air purifier is purchased generally as a small household appliance at a high price. Moreover, most of the harmful gases, such as smog, float on the upper layer of indoor air, such that it is necessary for the traditional air purifier to spend a relatively long time to purify the whole room. Therefore, to solve said problem, an air purifying function is added to lamps by a part of manufacturers at present, however, in general cases, a fan is taken as a driving source of wind energy to suck air and then exhaust purified air. But the problems, such as dust accumulation and noise during the operation of the fan are not beneficial for maintenance, and the structure is relatively complicated.

SUMMARY OF THE INVENTION

Based on this, it is necessary to provide an LED purifying and energy-saving lamp which has an air purifying function and a simple structure and is energy-saving and environment-friendly against the defects in the prior art.

An LED purifying and energy-saving lamp comprises a lamp body, a heat radiator, a light source assembly and an air purifying device, wherein the lamp body comprises a main body portion, an overflow table and a plurality of connecting block. The heat radiator, the light source assembly and the air purifying device are provided in the main body portion. The air purifying device is provided above the heat radiator. The light source assembly is provided inside the heat radiator. The upper part of the main body portion is connected to the bottom edge of the overflow table via the plurality of connecting blocks. The main body portion, the overflow table and the connecting blocks define a plurality of air outlets. A shunting spur is convexly provided at the bottom of the overflow table toward the interior of the main body portion. The shunting spur comprises a shunting surface connected to the bottom of the overflow table and an installing surface connected to a free end of the shunting surface, the shunting surface being arranged obliquely. The shunting convex tip is provided above the air outlets. The heat radiator is configured to diffuse heat generated in a working process of the light source assembly, and meanwhile heat air to form heat convection to make air rise, thereby causing outside air to flow into the main body portion. The air purifying device is configured to purify air inside the main body portion, and the shunting surface guides the purified air to be exhausted from the air outlets.

Further, the LED purifying and energy-saving lamp further comprises a driving power source which is provided inside the overflow table.

Further, the lamp body is arranged in a hollow tube-shaped structure, the overflow table has an annular cross section, and the outer diameter of the overflow table is less than that of the lamp body.

Further, the heat radiator comprises a support column and heat radiating ribs which are connected to the support column and are uniformly distributed around the support column by taking the support column as a center.

Further, the light source assembly further comprises a substrate and a lampshade, wherein the substrate is provided on the support column, the LED lamp is provided on the lower surface of the substrate, and the lampshade covers the LED lamp.

Further, the lower end surface of the support column is provided with a groove, the substrate is provided on the bottom surface of the groove, and the lampshade is provided in the groove and covers the LED lamp.

Further, the installing surface is arranged horizontally, and the heat radiator is fixed to the installing surface through a fastener.

Further, the air purifying device comprises an ozone aromatic base and a plasma base, wherein the ozone aromatic base and the plasma base are fixed to the installing surface through fasteners, and the plasma base is provided at a position where the air outlets are located.

Further, the LED purifying and energy-saving lamp further comprises a wall plate, wherein the overflow table is provided on the wall plate through a fastener.

Compared with the prior art, the LED purifying and energy-saving lamp of the present patent has an air purifying function while possessing an illuminating function by arranging the air purifying device, and in addition, the LED purifying and energy-saving lamp is simple in structure and convenient to maintain. The LED purifying and energy-saving lamp makes air enter into the lamp body and rise by using a heat convection principle and be processed by the air purifying device. The LED purifying and energy-saving lamp sufficiently utilizes heat energy emitted from LED lamp and is energy-saving, environment-friendly and applicable to be promoted and applied.

DETAILED DESCRIPTION OF THE PREFERRED EMBODIMENTS

To make the purpose, the technical solution and the advantages of the present utility understand more clearly, the present patent will be further described in details as below in conjunction with the drawings and the embodiments.

Figure 1:
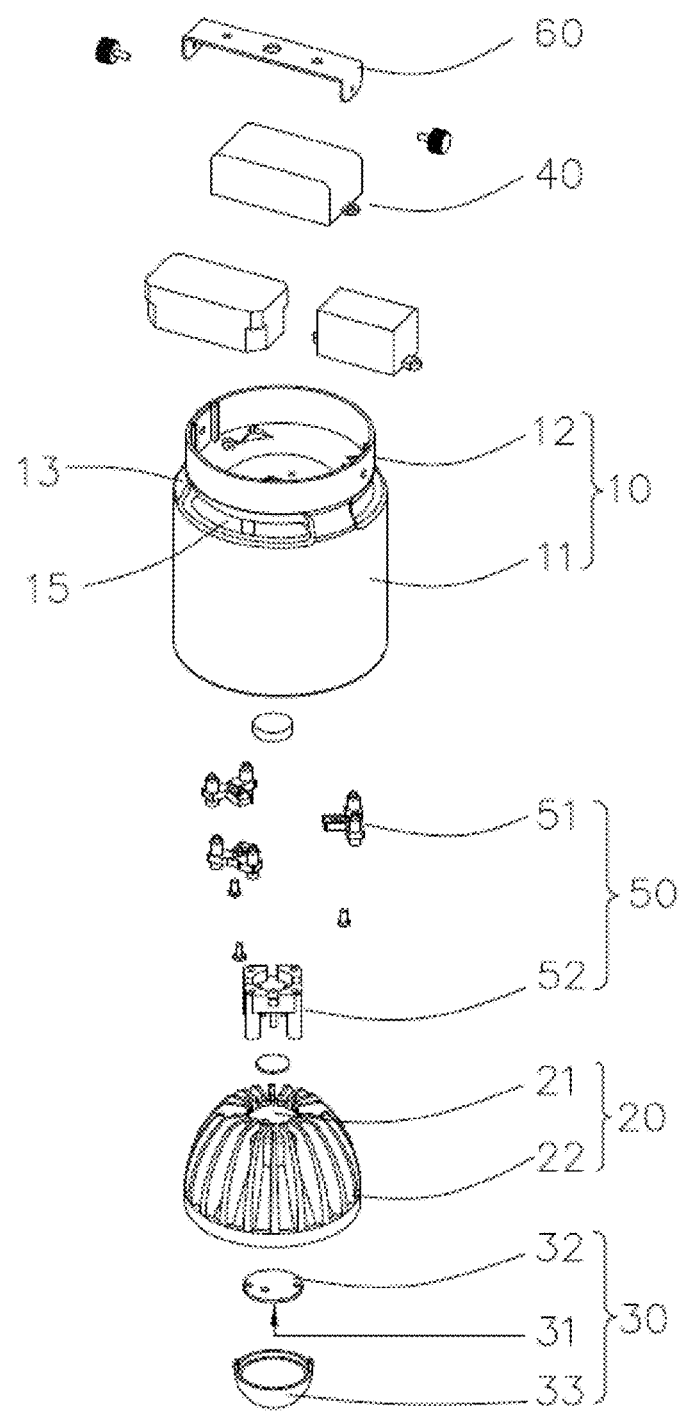
FIG. 1 is an exploded schematic drawing of the LED purifying and energy-saving lamp of the present patent.
Figure 2:
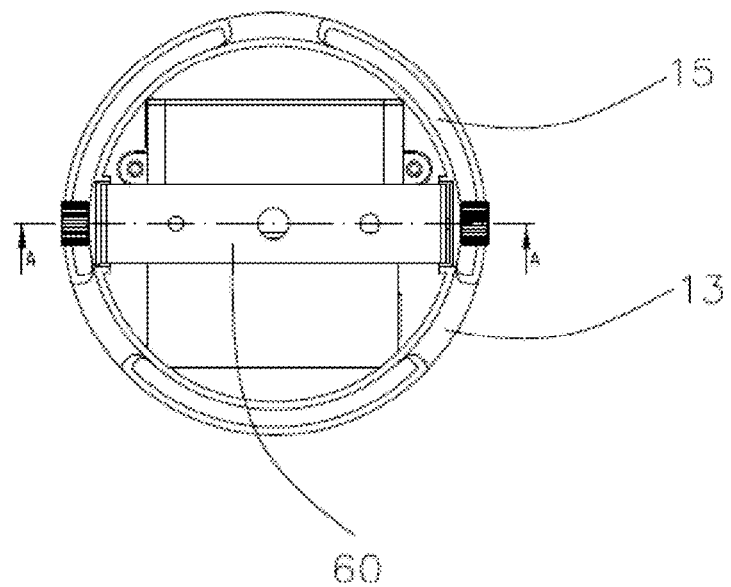
FIG. 2 is a top view of the LED purifying and energy-saving lamp as shown in FIG. 1.
Figure 3:
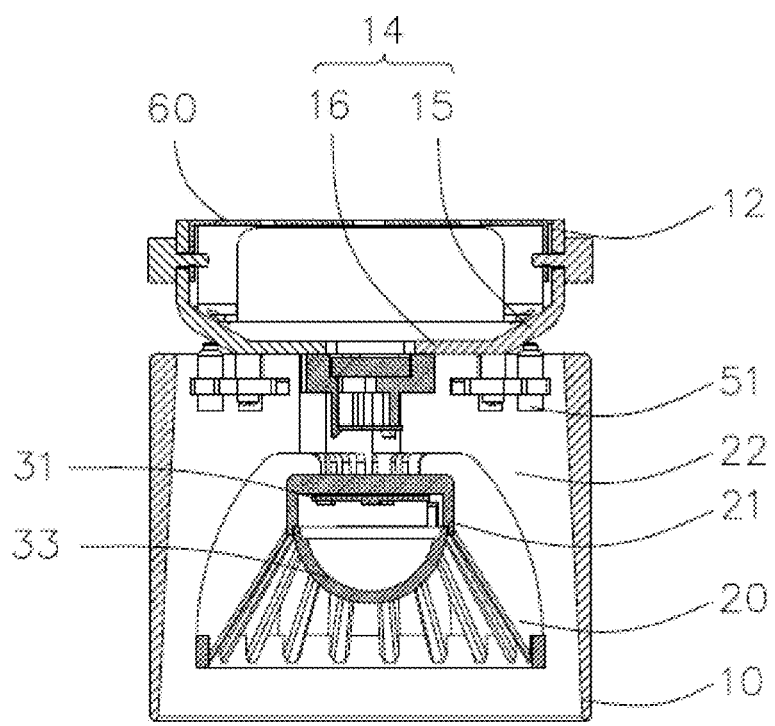
FIG. 3 is a sectional schematic drawing of the LED purifying and energy-saving lamp along a line A-A as shown in FIG. 2.

As shown in FIGS. 1-3, the present patent provides an LED purifying and energy-saving lamp for illuminating, which comprises a lamp body 10 and a heat radiator, a light source assembly 30, a driving power source 40, an air purifying device 50 and a wall plate 60 which are provided on the lamp body 10, wherein the driving power source 40 is electrically connected to the light source assembly 30. The air purifying device 50 is configured to purify air inside the lamp body 10. The heat radiator 20 is configured to diffuse heat generated in a working process of the light source assembly 30, and meanwhile heat air to form heat convection to make air rise, thereby causing outside air to flow through the lamp body 10.

The lamp body consists of two portions, namely a main body portion 11 and an overflow table 12, wherein the upper part of the main body portion 11 is connected to the bottom edge of the overflow table 12 through connecting blocks 13. The overflow table 12 is provided on the wall plate 60. The driving power source 40 is provided inside the overflow table 12. The heat radiator 20, the light source assembly 30 and the air purifying device 50 are provided inside the main body portion 11. The air purifying device 50 is provided above the heat radiator 20. The light source assembly 30 is provided inside the heat radiator 20.

The main body portion 11 is arranged in a hollow tube-shaped structure. The overflow table 12 has an annular cross section and is connected to the main body portion 10 in an integral forming manner. The outer diameter of the overflow table 12 is less than that of the main body portion 11. A plurality of air outlets 15 are formed among the main body portion 11, the overflow table 12 and the connecting blocks 13. A shunting spur 14 is convexly arranged at the bottom of the overflow table 12 towards the interior of the main body portion 11. The shunting spur 14 comprises a shunting surface 16 connected to the bottom of the overflow table and an installing surface 17 connected to a free end of the shunting surface 16. The shunting surface 16 is arranged obliquely and is provided above the air outlets 15. Due to the arrangement of the shunting surface 16 and the overflow table 12, the phenomenon of hot air accumulation can be eliminated to avoid that the service life of the illuminating lamp is affected because hot air is accumulated and difficult to diffuse.

The heat radiator 20 is provided on the installing surface 17 through a fastener and is arranged in an inverted cup shape. The heat radiator 20 comprises a support column 21 and a plurality of heat radiating fins 22 which are uniformly distributed around the support column 22 by taking the support column as a center. The heat radiating fins 22 are configured to enable heat generated from the light source assembly 30 to be diffused rapidly to improve the velocity of heat convection. The lower end surface of the support column 21 is provided with a groove. The light source assembly 30 comprises an LED lamp 31, a substrate 32 and a lampshade 33, wherein the substrate 32 is provided on the bottom surface of the groove of the support column 21, the LED lamp 31 is provided on the lower surface of the substrate 32, the lampshade 33 is provided inside the support column 21 and completely covers the LED lamp, and the LED lamp 33 is made of a light-pervious material.

The air purifying device 50 comprises an ozone aromatic base 51 and a plasma base 52, wherein the ozone aromatic base 51 and the plasma base 52 are fixed to the installing surface 17 through fasteners, the ozone aromatic base 52 is provided above the heat radiator 20, and the plasma base 51 is provided at a position where the air outlets 11 are located. The air purifier 50 is configured to ionize ambient air by the plasma base 51, thereby generating negative oxygen ions, and under the action of the negative ions, dust particles, smog, viruses, bacteria and other biological suspended pollutants become heavy ions and then descend, and meanwhile, neutralize positive ions in air to activate air, such that microparticles 2.5 (PM2.5) and floating dust under PM2.5 may be effectively removed, not only the environment is purified and a health care effect on a human body is achieved. The ozone aromatic base 52 is an ozone aromatic base and has the functions of refreshing air and sterilizing. It may be understood that, in other embodiments, the air purifying device 50 further comprises an ultraviolet lamp, a photocatalyst coating and the like.

When the illuminating lamp is turned on, heat emitted from the LED lamp 31 is diffused into the lamp body 10, air inside the lamp body 10 rises upon heating, and the volume of the heated air expands to reduce the density thereof, such that there is an upward flowing trend for the air. In addition, in the vertical tube-shaped lamp body 10, the rising air will be propelled by rising air newly generated below, such that air inside the lamp body 10 moves in an upward convection manner under driving and driven operations, the rising air is purified by the air purifying device 50, and the processed air is exhausted from the air outlets 11.

From the above, the LED purifying and energy-saving lamp of the present patent has an air purifying function while possessing an illuminating function by arranging the air purifying device 50, and in addition, the LED purifying and energy-saving lamp is simple in structure and convenient to maintain. The LED purifying and energy-saving lamp makes air enter into the lamp body and rise by using a heat convection principle and be processed by the air purifying device. The LED purifying and energy-saving lamp sufficiently utilizes heat energy emitted from LED lamp and is energy-saving, environment-friendly and applicable to be promoted and applied.

The above embodiments just express one implementation of the present patent, and the description is more specific and detailed, but will not be interpreted to limit the patent scope of the present patent. It should be noted that those skilled in the art may also make several variations and improvements on the premise of not departing from the conception of the present patent, all of which belong to the protection scope of the present patent. Therefore, the patent protection scope of the present patent should be subject to the attached claims.

What is claimed is:

1. An LED purifying and energy-saving lamp, comprising a lamp body, a heat radiator, a light source assembly and an air purifying device, wherein the lamp body comprises a main body portion, an overflow table and a plurality of connecting blocks; the heat radiator, the light source assembly and the air purifying device are provided in the main body portion; the air purifying device is provided above the heat radiator; the light source assembly is provided inside the heat radiator; the upper part of the main body portion is connected to the bottom edge of the overflow table via the plurality of connecting blocks; the main body portion, the overflow table and the connecting blocks define a plurality of air outlets; a shunting spur is convexly provided at the bottom of the overflow table toward the interior of the main body portion; the shunting spur comprises a shunting surface connected to the bottom of the overflow table and an installing surface connected to a free end of the shunting surface, the shunting surface being arranged obliquely; the shunting convex tip is provided above the air outlets; the heat radiator is configured to diffuse heat generated in a working process of the light source assembly, and meanwhile heat air to form heat convection to make air rise, thereby causing outside air to flow into the main body portion; and the air purifying device is configured to purify air inside the main body portion, and the shunting surface guides the purified air to be exhausted from the air outlets.

2. The LED purifying and energy-saving lamp according to claim 1, wherein the LED purifying and energy-saving lamp further comprises a driving power source which is provided inside the overflow table.

3. The LED purifying and energy-saving lamp according to claim 1, wherein the lamp body is arranged in a hollow tube-shaped structure, the overflow table has an annular cross section, and the outer diameter of the overflow table is less than that of the lamp body.

4. The LED purifying and energy-saving lamp according to claim 1, wherein the heat radiator comprises a support column and heat radiating ribs which are connected to the support column and are uniformly distributed around the support column by taking the support column as a center.

5. The LED purifying and energy-saving lamp according to claim 4, wherein the light source assembly further comprises a substrate and a lampshade, wherein the substrate is provided on the support column, the LED lamp is provided on the lower surface of the substrate, and the lampshade covers the LED lamp.

6. The LED purifying and energy-saving lamp according to claim 5, wherein the lower end surface of the support column is provided with a groove, the substrate is provided on the bottom surface of the groove, and the lampshade is provided in the groove and covers the LED lamp.

7. The LED purifying and energy-saving lamp according to claim 1, wherein the installing surface is arranged horizontally, and the heat radiator is fixed to the installing surface through a fastener.

8. The LED purifying and energy-saving lamp according to claim 4, wherein the installing surface is arranged horizontally, and the heat radiator is fixed to the installing surface through a fastener.

9. The LED purifying and energy-saving lamp according to claim 1, wherein the air purifying device comprises an ozone aromatic base and a plasma base, the ozone aromatic base and the plasma base being fixed to the installing surface through fasteners, and the plasma base being provided at a position where the air outlets are located.

10. The LED purifying and energy-saving lamp according to claim 1, wherein the LED purifying and energy-saving lamp further comprises a wall plate, wherein the overflow table is provided on the wall plate through a fastener.

* * * * *